(12) United States Patent
Tindal et al.

(10) Patent No.: US 6,387,400 B1
(45) Date of Patent: May 14, 2002

(54) PROCESS FOR PREPARING PHARMACEUTICAL COMPOSITIONS FOR USE WITH SOFT GELATIN FORMULATIONS

(75) Inventors: Stephen Charles Tindal, Lakeside; Christopher Clive Webster; Josephine Christine Ferdinando, both of Chippenham; Jacqueline Carol Lewis, Exmouth, all of (GB)

(73) Assignee: R.P. Scherer Technologies, Inc., Paradise Valley, NV (US)

( * ) Notice: Subject to any disclaimer, the term of this patent is extended or adjusted under 35 U.S.C. 154(b) by 0 days.

(21) Appl. No.: 09/649,947

(22) Filed: Aug. 29, 2000

(51) Int. Cl.$^7$ .................................................. A61K 9/48
(52) U.S. Cl. ....................... 424/455; 424/451; 424/452; 424/456
(58) Field of Search .................................. 424/451, 455, 424/456, 452, 454, 457, 453

(56) References Cited

U.S. PATENT DOCUMENTS 5,376,688 A    12/1994   Morton et al. ............... 514/786
5,912,011 A    6/1999    Makino et al. .............. 424/455

FOREIGN PATENT DOCUMENTS

| AU | B-81573/87 | 2/1991 |
| EP | 0 086 468 A2 | 8/1983 |
| EP | 0 178 436 B1 | 10/1990 |
| WO | WO 85/04106 | 9/1985 |

*Primary Examiner*—James M. Spear
(74) *Attorney, Agent, or Firm*—Andrew G. Rozycki; Donald D. Nickey

(57) ABSTRACT

The invention disclosed herein is a process for increasing the achievable concentration of a pharmaceutically active ingredient relative to fill composition viscosity for dosage units. The process is particularly useful in the preparation of soft gelatin capsules containing ibuprofen, naproxen, indomethacin, and acetaminophen, as the pharmaceutically active ingredient. As a result of the process, lesser quantities of composition ingredients other than the pharmaceutically active ingredient are needed to accomplish the same therapeutically effective dosage, thereby significantly increasing the concentration of the pharmaceutically active ingredient resulting in either a reduction in overall fill volume and dosage unit size or an increase in concentration of pharmaceutically active ingredient per dosage form.

22 Claims, No Drawings

PROCESS FOR PREPARING PHARMACEUTICAL COMPOSITIONS FOR USE WITH SOFT GELATIN FORMULATIONS

FIELD OF THE INVENTION

The invention disclosed herein relates to the field of oral pharmaceutical formulations. In particular, the invention relates to an improved process for preparing pharmaceutical compositions for use in soft gel formulations. The inventive process allows for a given dose of active ingredient to be placed in a smaller dosage form.

BACKGROUND OF THE INVENTION

Filled one piece soft gels have been widely known and used for many years and for a variety of purposes. Because softgels have properties which are different from conventional telescoping two-piece hardshell capsules, the soft gels are capable of retaining liquid fill material. Typically, softgels are used to contain orally consumable materials such as vitamins and pharmaceutical compositions in a liquid vehicle or carrier.

In general, not all liquids are suitable as vehicles or carriers for inclusion in softgels. For example, water, propylene glycol, glycerin, low molecular weight alcohols, ketones, acids, amines and esters cannot be used as a carrier in softgels by themselves since they interact with the gel and, if present, they can only be present in relatively small amounts.

Another limitation associated with softgels is the ability to incorporate a single dose of the pharmaceutically active ingredient in solution in an acceptable fill volume. Often, it is difficult to dissolve the pharmaceutically active ingredient in a volume of solvent small enough to produce a softgel which delivers the desired dosage amount, is economically appropriate and comfortable to ingest by the patient. Developing solvent systems for pharmaceutically active ingredients that neither significantly interact with the active ingredient nor the softgel casing itself, has proven a difficult art.

The chemical properties of certain types of drugs have necessitated the development of special solvent systems for soft gel dosage forms. Yu et al., Australian Patent Application No. 81573/87 discloses pharmaceutical formulations suitable for filling soft gels comprising acidic pharmaceutical agents and solvent systems, the solvent systems comprising 10% to 80% by weight polyethylene glycol, 1% to 20% by weight water and hydroxide ion species. The solvent systems dissolve the pharmaceutical agent, e.g., ibuprofen, in concentrations sufficient for use in soft gelatin capsules.

Increasing the concentrations of active ingredients in soft gelatin dosage forms and/or units without necessitating an increase in overall fill volume (and thereby increasing overall size of the dosage form) and/or without increased disintegration of the gelatin casing have proven difficult to accomplish in the art. Also problematic is the maintenance of a workable viscosity during such processes. Hence, there exists a need for improved processes in the pharmaceutical industry which produce pharmaceutical formulations in a manner which are more economical to manufacture and increase patient comfort.

SUMMARY OF THE INVENTION

The invention herein provides for a process whereby the concentration of pharmaceutically active ingredients in soft gelatin dosage units can be increased, thereby permitting the use of reduced overall fill volumes or, alternatively, higher concentrations of the active ingredient per dosage unit or form. Furthermore, undesirable interactions between the fill ingredients and the gelatin casing can be reduced or altogether avoided when using the process of the invention.

The process according to the invention increases the achievable concentration of a pharmaceutically active ingredient relative to fill viscosity for use in soft gelatin dosage units comprises the gradual and incremental addition of pharmaceutically active ingredient and a hydroxide ion source to polyethylene glycol.

Thus, there is disclosed a process of increasing the concentration of pharmaceutically active ingredient relative to fill composition viscosity for dosage units comprising the steps of a) combining a first portion of pharmaceutically active ingredient with substantially the total amount of polyethylene glycol to be used in the fill composition to form an initial suspension; b) mixing said suspension; c) adding a first portion of hydroxide ion source to the suspension; d) mixing the ingredients until dissolved to an extent sufficient to produce a workable viscosity; e) adding a second portion of the pharmaceutically active ingredient to the solution to form another suspension; f) mixing the suspension; g) adding a second portion of hydroxide ion source to the suspension; and h) mixing the ingredients until dissolved in solution; wherein said first and second portions of the pharmaceutically active ingredient and first and second portions of the hydroxide ion source are each less than the total amount of the respective ingredient used in the resulting fill composition. The resulting fill composition contains the pharmaceutically active ingredient in a solvent system which is particularly suitable in the preparation of soft gelatin capsules, and permits higher doses of active ingredient to be administered without increasing overall fill volume and thereby dosage unit size. Alternatively, the resulting fill compositions permit increased concentrations of pharmaceutically active ingredient to be used per dosage unit size.

Pharmaceutically active ingredients suitable for use in the invention include, but are not limited to, acidic compounds such as ibuprofen, naproxen, indomethacin and acetaminophen. A preferred pharmaceutically active ingredient is ibuprofen.

The solvent system prepared in accordance with the invention comprises polyethylene glycol (PEG) and a hydroxide ion source. Polyethylene glycols which can be used in accordance with the invention include those having a molecular weight range from about 200 Daltons to about 100,000 Daltons, and preferably ranging from about 400 Daltons to about 700 Daltons. Suitable hydroxide ion sources for use in the invention include sodium hydroxide (NaOH) and potassium hydroxide (KOH), more preferably potassium hydroxide.

According to the process of the invention, a first portion of the pharmaceutically active ingredient is combined with polyethylene glycol and mixed together to form a first suspension. A first portion of hydroxide ion source is then added and the ingredients mixed to the extent sufficient to produce a workable viscosity. A second portion of pharmaceutically active ingredient is added and mixed to form a second suspension, and a second portion of hydroxide ion source is added to the suspension to form a solution. The first and second portions of the pharmaceutically active ingredient and hydroxide ion source, respectively, together comprise the total amount of each ingredient used to prepare the liquid fill composition.

In a further embodiment, the process can further comprise additional steps of adding the pharmaceutically active ingredient and adding hydroxide ion source. Accordingly, three or more portions each of the pharmaceutically active ingredient and hydroxide ion source can be used in the process of the invention.

The invention also provides for a soft gelatin capsule containing a fill composition prepared according to the process of the invention.

The invention further provides for fill composition for gelatin capsules comprising:
a) an acidic pharmaceutically active ingredient having a concentration of at least 50% by weight, preferably about 55% by weight, of the total fill composition;
b) polyethylene glycol; and
c) a hydroxide ion source having a concentration of about 5.5% or less by weight of the total fill composition.

Preparing a liquid fill composition according to the process of the invention increases the achievable concentration of pharmaceutically active ingredient in the solvent system for a given viscosity. One advantage of the invention is that lesser quantities of the ingredients for the fill composition other than the pharmaceutically active ingredient can be used. For example, smaller quantities of polyethylene glycol are needed for the same amount of active ingredient. Hence, the same dosage of pharmaceutically active ingredient can be accomplished using smaller overall fill volume as compared to previous techniques. The invention can be used to render manufacturing processes more economical and improves patient comfort by reducing capsule size or the number of dosage units needed for treatment.

Another advantage of the invention is that since the process involves smaller total quantities of hydroxide ion source, the potential for degradation of the soft gelatin material by the hydroxide ions is significantly reduced. Accordingly, the storage capabilities and shelf-life of the product are improved.

DETAILED DESCRIPTION OF THE INVENTION

As used herein, the term "soft gelatin dosage unit" is intended to encompass any dosage unit and/or form which employs a gelatin or gelatin-like casing. Numerous casing materials have been proposed for soft capsules including gums, carrageenans, hydroxypropylated starches, celluloses, and the like. As used herein, the term "soft gelatin dosage unit" means a dosage form constructed of mammalian gelatin, fish gelatin, gums, guars, carrageenans, modified starches and the like.

The terms "fill" and "fill composition" are meant to describe that portion of a dosage unit (e.g., pill, capsule, and the like) that is encased or otherwise contained within the outermost portion. When used in reference to soft gelatin dosage units, the terms refer to compositions encased inside the gelatin containment.

As used herein, the phrase "workable viscosity" refers to the lack of substantive and/or disadvantageous resistance, or increase in effort required, in the physical agitation necessary to combine the ingredients during the process of the invention.

The general steps of the process of the invention comprise the gradual and incremental addition of the pharmaceutically active ingredient and hydroxide ion source to the polyethylene glycol in order to balance of ingredients in the solvent system with respect to the active ingredient during the process thereby achieving higher concentrations of pharmaceutically active ingredient relative to fill viscosity. In the first step of the process, a first portion of pharmaceutically active ingredient is combined with all of the polyethylene glycol or substantially all of the polyethylene glycol, to be used in the fill composition and mixed to form an initial suspension. Subsequently, a first portion of hydroxide ion source is added to the suspension and the ingredients are mixed until dissolved to an extent sufficient to produce a workable viscosity. To this mixture, a second portion of pharmaceutically active ingredient is added and mixed. Then, a second portion of hydroxide ion source is added and the ingredients dissolved until the resultant liquid fill composition is obtained.

The gradual and incremental addition of the total pharmaceutically active ingredient and hydroxide ion source amounts, respectively, in the interchanging manner as described produces a solvent system for the active ingredient which balances the interaction between the active ingredient and the viscosity of the fill in such a manner that accommodates higher concentrations of the active ingredient per total volume of fill without creating excessively high viscosities. Otherwise, preparations of such high concentrations of pharmaceutically active ingredient in this system would result in suspensions too viscous to stir on a commercial and/or practical scale when using conventional equipment. As a result, it would not accommodate the addition of the hydroxide component. Those skilled in the art will appreciate that homogeneous mixtures are critical in the pharmaceutical art, and that adequate mixing or agitation is required to accomplish homogeneous mixtures suitable for encapsulation in gelatin capsules and the like.

The relative amounts of pharmaceutically active ingredient and hydroxide ion source which are added each time during the process, as well as the number of addition steps for each ingredient, can vary provided a workable viscosity is maintained throughout the process. The active ingredient can be added in a proportionate amount to the total active ingredient in a range from about 10% to about 90% of the total amount (100%) of the active ingredient to be added. Likewise, each addition of hydroxide ion source can be in an amount ranging from about 10% to about 90% of the total hydroxide ion source to be added. The amounts of each ingredient added during the process need not be identical. Accordingly, various combinations of number and amount of ingredient repetitions are possible according to the invention provided a workable viscosity is maintained throughout the process. The quantity of each portion of ingredient added will vary according to the chemical properties of active ingredient, the interaction between the ingredients, and the reaction parameters employed in the process.

In a "two-step addition" process embodiment, half of the active ingredient can be added followed by half of the hydroxide ion source in each respective addition step, for example. Alternatively, half of the active ingredient can be added, followed by the addition of a third of the hydroxide ion source, and subsequently the other half of the active ingredient and the remaining two-thirds of the hydroxide ion source. Three or more addition steps can also be used for each respective ingredient in the process.

Pharmaceutically active ingredients useful in the present invention include acidic compounds such as ibuprofen, naproxen, indomethacin, and acetaminophen. A preferred pharmaceutically active ingredient is ibuprofen.

The hydroxide ion source used in the invention is generally present in an amount of about 5.5% or less of the total fill composition volume, since degradation of gelatin casings tends to occur above about 5.5% hydroxide content. Suitable hydroxide ion sources include, but are not limited to, potassium hydroxide and sodium hydroxide. A preferred hydroxide ion source is potassium hydroxide. Most preferred for use in the invention is a 50% aqueous solution of potassium hydroxide. Potassium hydroxide is preferred as the hydroxide ion source because it enhances the solubility of acidic pharmaceutical ingredients more than sodium hydroxide and is less likely to result in precipitation over a wide variety of concentrations at lower temperatures.

The initial suspension used in the process typically contains the total amount of polyethylene glycol which will be used for the fill composition. Polyethylene glycols (PEG) which can be used in accordance with the invention include those having a molecular weight range from about 200 Daltons to about 100,000 Daltons, and preferably ranging from about 400 Daltons to about 700 Daltons.

In an alternative embodiment, polyethylene glycol derivatives can be used in accordance with the invention. Suitable polyethylene glycol derivatives include, but are not limited to, polyethylene glycol ethers of alcohols and co-polymers of polyethylene glycol. An example of a polyethylene glycol ether of an alcohol is tetraglycol, which is a polyethylene glycol ether of tetrahydrofurfuryl alcohol.

In an alternative embodiment, other solvent systems can be used in accordance with the invention. For example, suitable solvent systems include those described in Makino et al. U.S. Pat. No. 5,912,011 and Morton et al. U.S. Pat. No. 5,376,688, the entire texts of which are incorporated herein by reference.

Additional ingredients which enhance the solubility of the active pharmaceutical ingredient in polyethylene glycol can be used as well, provided such ingredients are present only in amounts sufficient to preserve the desired viscosity and that do not degrade the gelatin capsule. Examples of additional ingredients include, but are not limited to, glycerin, propylene glycol, and polyvinylpyrrolidone, and combinations thereof. The amount and combination of additional ingredient(s) used will vary according to the chemical properties of the other ingredients used in the process.

Conventional additives can be used in conjunction with the process of the invention as well, including but not limited to, preservatives, stabilizers, wetting agents, coloring agents, and the like.

The chemical interaction between the pharmaceutically active ingredient and the polyethylene glycol/potassium hydroxide solvent system as applied according to the process of the invention are substantially optimized producing the capability of higher concentrations of active ingredient relative to a given viscosity of the PEG/KOH solvent system. Throughout the process of the invention, the viscosity of the composition at each stage is controlled by virtue of the chemical properties of each ingredient with the other in conjunction with particular incremental proportions added.

EXAMPLE 1

Comparison Between Processes for Preparing Fill Compositions Containing Ibuprofen Two pharmaceutical compositions suitable for use in soft gelatin capsules were prepared according to two different processes. One process was conducted in accordance with a previously known method (Process 1), whereas a second process was carried out in accordance with the invention (Process 2). Both processes prepared compositions (Formulas 1 and 2, respectively) containing ibuprofen as the pharmaceutically active ingredient which were suitable for use in soft gel capsules.

Process 1 was carried out as follows:

Initially, 20.4 kg of PEG 600 was added to a heated mixing vessel and stirred until a temperature of 350° C. or less was obtained. To the PEG 600 in the mixing vessel was added 19.6 kg of ibuprofen. The combination was mixed to form a slurry. Subsequently, 5.0 kg of KOH solution (50% by weight KOH/50% by weight water) was slowly added to the slurry while maintaining a solution temperature below 5020 C. to form a clear solution. A total batch size of 45 kg was prepared.

Process 2 was carried out according to the invention as follows:

Initially, 15.0 kg of PEG 600 was added to a heated mixing vessel and stirred until a temperature of 35° C. or less was reached. Half (12.5 kg) of the total amount of ibuprofen to be used was added to the PEG 600 in the vessel and the combination was mixed to form a slurry. One third (1.7 kg) of the total amount of KOH solution (50% by weight KOH/50% by weight water) was added to the vessel while maintaining a temperature of less than 50° C. The remaining half (12.5 kg) of the ibuprofen was added to the mixture and mixed to form a slurry. The remaining two-thirds (3.3 kg) of the KOH solution was added while maintaining a temperature below 50° C. to form a clear solution. The total batch size prepared was 45 kg.

It was observed that in a separate experiment that when the total amount of ibuprofen (25 kg) (as found in the reduced fill composition of Process 2) was added to the PEG 600, it produced a mixture which was so thick and high in viscosity that the resulting suspension was unworkable.

The quantities of each ingredient used in Process 1 and 2 and resulting concentration of active ingredient (ibuprofen) are summarized below:

TABLE 1

Comparison of Prepared Ibuprofen Fill Compositions

| Ingredient | Process 1 | Process 2 |
| --- | --- | --- |
| Ibuprofen | 19.6 kg | 25.0 kg |
| PEG 600 | 20.4 kg | 15.0 kg |
| KOH | 5.0 kg | 5.0 kg |
| TOTAL | 45.0 kg | 45.0 kg |
| Ibuprofen Concentration | 43.5% | 55.6% |

As can be seen from the resulting data in Table 1, a significantly higher concentration of ibuprofen, a 12.1% increase in comparison for the same total fill volume of 45.0 kg, was obtained when preparing the fill composition in accordance with the invention. Furthermore, a weight ratio of ibuprofen to total fill 0.556 or 5:9 was obtained using the process according to the invention. In contrast, the prior art process resulted in an ibuprofen to fill weight ratio of 0.435.

Industrial Applicability

When the process of the invention is used in manufacturing soft gelatin dosage units, the solubilization of pharmaceutically active ingredients such as ibuprofen can be significantly increased thereby permitting smaller fill volumes for a given dosage to be employed. Accordingly, smaller capsule sizes or fewer capsules need to be produced, thereby allowing more economical manufacture and improving patient comfort and compliance.

The complete disclosures of all patents, patent applications, and publications are incorporated herein by reference as if each were individually incorporated by reference. The invention has been described with reference to various specific and preferred embodiments and techniques. However, it should be understood that reasonable variations and modifications are possible from the foregoing disclosure without departing from either the spirit or scope of the present invention as defined by the claims.

What is claimed is:

1. A process for increasing the concentration of a pharmaceutically active ingredient relative to fill composition viscosity for dosage units comprising the steps of:
    a) combining a first portion of a pharmaceutically active ingredient with substantially the total amount of polyethylene glycol to be used in the fill composition to form an initial suspension, said polyethylene glycol having a molecular weight ranging from about 200 Daltons to about 100,000 Daltons;
    b) mixing said suspension;
    c) adding a first portion of hydroxide ion source to the suspension;
    d) mixing the ingredients until dissolved in solution;
    e) adding a second portion of pharmaceutically active ingredient to the solution to form another suspension;
    f) mixing the suspension;
    g) adding a second portion of hydroxide ion source to the suspension; and
    h) mixing the ingredients until dissolved in solution;
    wherein said first and second portions of the pharmaceutically active ingredient and first and second portions of the hydroxide ion source are each less than the total amount of the respective ingredient used in the resulting fill composition.

2. The process of claim 1 wherein the dosage unit comprises a soft gelatin capsule.

3. The process of claim 1 wherein the pharmaceutically active ingredient is an acidic pharmaceutical compound.

4. The process of claim 1 wherein the pharmaceutically active ingredient is selected from the group consisting of ibuprofen, naproxen, indomethacin, and acetaminophen.

5. The process of claim 4 wherein the pharmaceutically active ingredient is ibuprofen.

6. The process of claim 1 wherein the pharmaceutically active ingredient is present in the resulting composition in a weight ratio of pharmaceutically active ingredient to total fill composition of at least 1:2.

7. The process of claim 6 wherein the pharmaceutically active ingredient is present in the resulting composition in a weight ratio of pharmaceutically active ingredient to total fill composition of about 5:9.

8. The process of claim 1 wherein the polyethylene glycol has an average molecular weight of between about 400 to about 700 Daltons.

9. The process of claim 1 wherein polyethylene glycol is present in the resulting composition in a ratio of polyethylene glycol to total fill volume of about 1:3.

10. The process of claim 1 wherein said hydroxide ion source is selected from the group consisting of sodium hydroxide and potassium hydroxide and mixtures thereof.

11. The process of claim 9 wherein said hydroxide ion source is potassium hydroxide.

12. The process of claim 11 wherein potassium hydroxide is present in the resulting composition in less than about 5.5% by weight of the total fill composition.

13. The process of claim 1 wherein the pharmaceutically active ingredient is incrementally added in at least three portions during the process, each portion being less than the total amount of pharmaceutically active ingredient used in the resulting fill composition.

14. The process of claim 1 wherein one of the first and second portions of pharmaceutically active ingredient is less than about 90% by weight of the total pharmaceutically active ingredient added.

15. The process of claim 13 wherein each of the first and second portions of pharmaceutically active ingredient are about 50% by weight of the total pharmaceutically active ingredient added.

16. The process of claim 1 wherein the hydroxide ion source is incrementally added in at least three portions during the process, each portion being less than the total amount of hydroxide ion source used in the resulting composition.

17. The process of claim 1 wherein one of the first and second portions of hydroxide ion source is less than about 90% by weight of the total amount of hydroxide ion source added.

18. The process of claim 16 wherein one of the first and second portions of hydroxide ion source is about two-thirds by weight of the total amount of hydroxide ion source added.

19. A soft gelatin capsule containing a fill composition produced by the process of claim 1.

20. The soft gelatin capsule of claim 19 wherein the pharmaceutically active ingredient is an acidic pharmaceutical compound.

21. The soft gelatin capsule of claim 20 wherein the pharmaceutically active ingredient is selected from the group consisting of ibuprofen, naproxen, indomethacin, and acetaminophen.

22. The soft gelatin capsule of claim 21 wherein the pharmaceutically active ingredient is ibuprofen.

* * * * *